United States Patent [19]
Smith

[11] 3,943,993
[45] Mar. 16, 1976

[54] LOW TEMPERATURE STORAGE OF SURFACE ATTACHED LIVING CELL CULTURES

[76] Inventor: Kendall O. Smith, 133 Trillium Lane, San Antonio, Tex. 78213

[22] Filed: May 3, 1974

[21] Appl. No.: 466,909

[52] U.S. Cl............................. 165/2; 62/64; 128/1 R; 195/1.8
[51] Int. Cl.²........................................ F25B 13/00
[58] Field of Search................. 62/62, 64, 373, 376; 195/1.7, 1.8; 165/2, 61; 128/1 R

[56] References Cited
UNITED STATES PATENTS
3,303,662    2/1967    Moline.................................... 62/62

OTHER PUBLICATIONS
Polge, Smith and Parkes, Nature, London, 164:666, (1949).
Shimada and Ashina, Cryobiology, 9:51–56, (1972).
Vos and Kaalen, Cryobiology, 1:249–260, (1965).
Ashwood-Smith, Warby, Becker and Connor, Cryobiology, 9:311, (1972).
Scherer and Hoogasian, Proc. Soc. Exp. Biol. Med., 87:480–487, (1954).
Farrant, Nature, London, 205:1284–1287, (1965).
Paul, Cell and Tissue Culture, 4th Ed. pp. 308–315, The Williams and Wilkens Co., Baltimore, (1970).
Wasley and May, Animal Cell Culture Methods, pp. 137–144, Blackwell Sci. Publications, Oxford and Edinburgh, (1970).
Meryman, Annals of the New York Academy of Sciences, 85:503–509, (1960).
Tissue Culture Methods and Applications, ed. by P. F. Kruse, Jr. and M. K. Patterson, Jr., N. Y. and London, Academic Press, 1973, pp. 270–274.

*Primary Examiner*—William F. O'Dea
*Assistant Examiner*—Ronald C. Capossela
*Attorney, Agent, or Firm*—Watson, Cole, Grindle & Watson

[57] ABSTRACT

A process is described in which surface attached living cell cultures are treated, cooled, stored and revived in such a manner as to retain their viability and their adherence to culture surfaces.

21 Claims, No Drawings

LOW TEMPERATURE STORAGE OF SURFACE ATTACHED LIVING CELL CULTURES

BACKGROUND OF THE INVENTION:

1. Field of the Invention

This invention relates to the field of preserving living cell cultures. More particularly a method is provided which allows surface-attached cell cultures to be cooled, stored and later revived without greatly disturbing their adherence to the original surfaces upon which they were attached and without destroying their capability for being revived as living cell cultures.

2. Description of Prior Observations

Polge, Smith and Parkes, *Nature, London* 164:666 (1949) discovered that bull spermatozoa can be preserved for long periods of time by freezing suspended cells in the presence of 5-10% glycerol. Since their discovery many workers have used modifications of this technique for the preservation of living cells of various types. Subsequently, a technology developed which has been aimed at improving the efficiency with which suspensions of living cells can be revived after storage in the frozen state.

While Shimada and Ashina, *Cryobiology* 9:51-56 (1972) have studied the freezing and thawing of surface-attached living cells, they were principally interested in microscopically observing individual HeLa cells which were attached to cover-slips during the freezing the thawing processes in the absence of the chemicals usually employed for long term storage of cells in the frozen state. The storage aspects of frozen cells were not studied by Shimada and Ashina, rather, they thawed the cells within minutes after freezing, at different rates and with and without ice crystals "seeding". The physical effects of these treatments on the morphology of the cells was observed.

Variables which have been studied for storing suspended cells include incorporation of different chemical components into the storage medium (See Vos and Kaalen, *Cryobiology* 1:249-260 (1965) and Ashwood-Smith, Warby, Becker and Connor, *Cryobiology* 9:311 (1972)), the concentration of these components, the rate at which the temperature is lowered during the initial cooling process, the temperature at which cells are stored and the rate at which cells are warmed during revival. Scherer and Hoogasian, *Proc. Soc. Exp. Biol. Med.* 87:480-487 (1954), using glycerol in their storage medium, did some of the first experimental work to determine optimal conditions for storing suspended cells derived from cell cultures. Later, dimethyl sulfoxide (DMSO) was found useful for storing suspended cells at low temperatures (See Farrant, *Nature, London* 205:1284-1287 (1965). Glycerol and DMSO are, at the present time, probably the most generally used chemicals employed in the various media utilized for storing suspended cells derived from cell cultures (see the discussion by Paul, *Cell and Tissue Culture*, 4th Ed., pp. 308-315, The Williams and Wilkins Company, Baltimore (1970) and that by Wasley and May, *Animal Cell Culture Methods*, pp. 137-144, Blackwell Scientific Publications, Oxford and Edinburgh (1970)). About 5% to about 15% concentrations of glycerol or DMSO are now most commonly used, although Scherer and Hoogasian successfully used glycerol at concentrations up to 30%. The latter workers also reported successful storage of both HeLa and L cell cultures after rapid cooling; however, slow cooling at about one centigrade degree per minute is now generally favored and practiced. In fact, Meryman, *Annals of the New York Academy of Sciences*, 85:503-509 (1960) stated that, except for mammalian erythrocytes, "rapid freezing does not appear to work for the majority of animal tissues". Meryman further stated "we must abandon for the time being the rapid freezing approach which, whether because of intracellular crystal growth or some other undetermined mechanism, simply does not work". Cells of different kinds seem to vary in their sensitivity to rapid cooling, as well as to other variables in the storage process. Slow cooling, at the rate of about one centigrade degree per minute, gives satisfactory results for storing many kinds of suspended cells derived from cell cultures, by the processes now practiced, and is the method now most generally used.

With minor variations, freezing and storage of cultured cells is presently accomplished in the following manner: Cells adhering to and growing on vessel surfaces are washed with physiological saline and are detached from such surfaces by mechanical means (shaking or scraping) and/or by the use of enzymes and a chelating agent (such as EDTA). The cell suspension is usually centrifuged, the liquid phase containing the enzymes or chelating agent discarded (some workers eliminate this step, but it is recommended for optimal results) and the cells re-suspended in a liquid suitable for freezing (usually this contains about 5% to about 15% DMSO or glycerol). The cells are kept at 0°-4°C while a sample is counted in a hemacytometer and then the volume of the liquid is adjusted to give the desired cell concentration (usually about $2 \cdot 10^6$ cells/ml). Measured volumes of the cell suspension are placed into multiple ampoules (cell suspensions must, of course, be continually agitated during this period to keep them in a homogeneous suspension). The ampoules are then sealed, (usually with a hot torch), frozen slowly (special equipment is usually required) and maintained at a storage temperature of $-70°C$ or below until needed. The frozen cell suspensions are then thawed rapidly, centrifuged, the liquid phase containing the storage medium is discarded, the cells are resuspended by agitation and the cells placed into appropriate culture vessels to grow. Cultures are divided after cell crowding occurs and, when a sufficient number of cells have developed in a sufficient number of the appropriate type of culture vessels, they are used for specific purposes such as virus experimentation, isolation of viruses from clinical specimens, titration of viruses, virus production, or further cell propagation. Summarizing, the methods for cell freezing and storage now commonly used involve the following manipulations: detachment from the culture surface by mechanical agitation, scraping or enzyme treatment, centrifugation to remove the enzyme, resuspension in storage medium, continuous agitation, cell counting, adjustment of the cell concentration, dispensing into ampoules, sealing the ampoules, slow freezing, thawing, re-centrifugation to remove the storage medium, continuous agitation, cell counting, adjustment of the cell concentration, dispensing into ampoules, sealing the ampoules, slow freezing, thawing, re-centrifugation to remove the storage medium, resuspension by agitation, and dispensing into new culture vessels for cell growth. These manipulations, in addition to being numerous and likely to shock or damage cells, are time consuming, require enzymes, and/or chelating agents, require a centrifuge, require a device for controlled freezing, require special sealable ampoules for storage and require the use of new culture vessels for growth of the revived cells. When done expertly under the best of circumstances recovery rates of up to 95% viable cells have been attained. Figures less than this are frequently obtained because it is difficult to achieve uniformly optimal performance at every one of the many steps involved. Poor recovery of viable cells in some cases is probably due to a peculiar susceptibility of certain cell types to one or more of these manipulations.

SUMMARY OF THE INVENTION

In accordance with the present invention the foregoing shortcomings of prior art methods and the difficulties encountered in the use thereof are substantially eliminated through the use of a process for cooling, storing and reviving surface attached living cells which includes the steps of (1) exposing living cells which are attached to a surface of a storage vessel to a storage medium which is relatively non-toxic to such cells and which is compatible therewith during cooling to a temperature below 0°C, storage and subsequent warming processes; (2) cooling the storage vessel and the surface attached living cells therein to a storage temperature below 0°C effective for arresting the metabolism of the cells; and (3) storing said vessel and said surface attached cells at said storage temperature for an extended period of time. In its broader aspects the invention also is directed to a frozen package of cellular material which comprises: (1) a storage vessel having an internal surface; (2) a quantity of living cells which are surface attached to said surface of said vessel; and (3) at least a sufficient quantity of a storage medium to wet the outer surfaces of said cells disposed in coating relationship thereto. In accordance with the invention the medium is relatively non-toxic to the cells and is compatible therewith during cooling to a temperature below 0°C, storage and subsequent warming processes, and the entire package has a temperature below 0°C effective for arresting the metabolism of the cells.

In its more specific and preferred aspects, the processes and package of the invention include the use of a storage medium which contains between about 5 and about 40% of either dimethyl sulfoxide, glycerol or ethylene glycol. A cooling rate of about 1°C per minute is particularly effective and storage temperatures between about 0°C and −200°C have been found to be highly useful. A particularly useful storage temperature is about −70°C.

The present invention contemplates, subsequent to the storage step, the warming of the vessel and the surface attached cells therein sufficiently to thaw the cells whereby the same may be utilized in the usual manner and for conventional purposes.

The process of this invention is most clearly distinguishable from the living cell storage art now practiced in that it is concerned only with the systematic preservation and storage in place of cells which adhere to surface within the culture vessels, not with the preservation and storage of suspended cells. In addition, conditions have been found for rapidly cooling surface adhering living cell cultures in media containing 5–30% concentrations of DMSO so that excellent recovery of the surface adhering living cells can be achieved following storage.

It is a primary object of this invention to provide a new, improved and simplified method for preserving and storing living cell cultures at low temperatures.

One of the important objectives of this invention is to preserve surface attached living cells in situ (in their cultured position) and thus minimize cell manipulation, with the associated shock and damage to the cells. By the process of this invention, shaking, scraping, agitation and exposure to enzymes or other chemicals normally required for suspending the cells are avoided, so that revived cells require less time to recover from the shock associated with storage. In fact, cells stored according to the process of this invention frequently can be used for viral studies or other experimentation immediately after thawing. If the preferred embodiments of this invention are followed, stored cells remain attached to the surfaces of the vessels and resemble healthy cells almost immediately after warming. Pseudopods usually remain extended and there is little evidence that the cells have been stored.

A further objective of this invention is to eliminate the need for centrifugation to remove dispersing agents or storage medium and the required use of sophisticated equipment associated with controlled temperature slow cooling (such as a controlled temperature unit made by Canal Industrial Corporation, Bethesda, Md.).

It is a purpose of this invention to provide conditions for treating, cooling and storing living cell cultures, such that the rate of initial cooling and the requirement for very low storage temperatures are less critical for satisfactory revival of the living cells. According to the present art, cells are usually cooled slowly under carefully controlled conditions and stored at temperatures of −70°C or less in order to achieve satisfactory recovery of living cells.

Another purpose of this invention is to eliminate the need for two sets of vessels required to achieve cell storage according to the art now practiced, i.e., (1) sealable ampoules for freezing and storage and (2) new culture vessels for the revived cells. This constitutes a saving of materials and a consequent saving in the cost of cell storage.

A further objective of this invention is to allow storage of living cell cultures directly in the vessels most suitable or convenient for their eventual use after revival. In this way, sudden, unpredicted needs for cell cultures (as in clinical laboratories where specimens for inoculation or infectious agents arrive unexpectedly) can be readily met without practicing the wasteful and costly procedure of keeping cells perpetually available in the particular type of vessels most suitable for immediate use. This latter procedure is presently followed and consequently many cell cultures must be eventually discarded when they are not used. According to the process of this invention, only the exact number of vessels, the exact types of vessels, and the specific cell types actually required at a particular time need be withdrawn from storage and revived for use. Although these benefits of the present invention are particularly enjoyed by the ultimate user of cells, this technique will also be especially useful to commercial suppliers who now systematically over-produce cell cultures in order to guarantee prompt delivery to customers who unexpectedly increase their demands. Such predictable, calculated waste by the commercial supplier is costly and this cost is, of course, passed along to the user.

Another objective of this invention is to improve the uniformity of living cell cultures available for use. Serial propagation of cell cultures inevitably leads to changes in the genetic characteristics of most cells and biological aging of cell lines which sometimes have finite life expectancies. Further in the prior art methods described above, there is a perpetual risk of contamination with infectious agents from different lots of serum and trypsin or as a result of manipulation by technicians. The inevitable consequence of this procedure is a variation in the results obtained when serially propagated, constantly changing cells are used experimentally or for purposes such as vaccine production. According to the process of the present invention, cells of one lot are distributed under identical conditions into the vessels in which they will actually be used, then stored and retrieved as truly replicate cell cultures. This provides uniquely uniform materials for revival and use in experiments or projects over long periods of time.

In the past, some have sought to minimize inevitable changes in serially propagated cells by periodically discontinuing serial propagation of certain cell culture lines and reviving stored aliquots of antecedent cultures (frozen in suspension) for further serial propagation and use. Another objective of the present invention is to eliminate the necessity of serially propagating a specific cell lot following its revival from the frozen state and prior to its use. Multiple cell cultures are thus available for use, each of whose culture history is exactly the same as every other culture and each of which can be revived at any convenient time. Thus, the biological age of cells in multiple vessels can be artificially arrested at the time they are stored, and the cells be made perpetually available for revival and continuation of the "biological clock" or aging process, to proceed to the exact point selected by the experimentalist. This invention fulfills a practical need for uniformity of cell cultures long recognized but previously difficult, if not impossible to achieve.

Cells adhering to surfaces within replicate culture vessels can, of course, be treated with any chemical, or infected with infectious agents prior to their storage, then cooled and stored until it is convenient to revive them. In this way, uniformly treated cells can be made perpetually available for convenient revival, for example, as control infected cultures or as a convenient source of freshly replicating infectious agents. Similarly, cell cultures can be treated physically (as by radiation) to alter their characteristics and be conveniently stored and revived when needed. It is therefore, an objective of this invention to provide a means for storage and revival of multiple replicate cell cultures which have been treated identically with chemicals, infectious agents or physical stress. The uniformity of cell treatment is a benefit permitted by this invention perhaps as important to some experimentalists as the uniformity of the stored cells themselves.

Another objective of this invention is to permit testing of sample replicate primary cell cultures before the remainder of a stored lot of cells is used for experimentation or for purposes such as viral vaccine production. The term "primary cell culture" is defined as the first out-growth of cells, in culture, from tissues obtained directly from the animal. Removal of these cells from vessel walls and re-culturing them constitutes a "passage" of the cells, therefore they can no longer be regarded as primary. There are, in specific cases, legal restrictions against the use of other than primary cells for viral vaccine production. Therefore, viral vaccine manufacturers usually proceed with the many operations required for vaccine production in primary cell cultures at the same time that governmentally required purity and safety tests on sample uninoculated (control) cell cultures are being accomplished. Sometimes vaccine is almost ready for market before the required tests on control cultures are completed. This procedure is costly to the producer if the control cell cultures are found to be contaminated with infectious agents or if the control cells otherwise fail to meet governmental standards concerning purity and safety. According to the process of the present invention, the main body of a primary cell lot can be stored in a stable condition until replicate control cultures from that lot have been thoroughly tested to insure that the cells are suitable for use. This can enable the manufacturer to avoid expensive processing of vaccine lots which must later be discarded when the uninoculated control cell cultures fail to meet required standards.

A further objective of this invention is to make possible the more satisfactory transport of living, surface attached cell cultures in the same culture vessels in which they will ultimately be used (for the greater convenience of the recipient) by transporting them in an extremely stable condition, i.e., in the cooled state and in a condition such that changes in position of the culture vessels cause no difficulties. Transport of surface attached living cells now involves exposure to deleterious or lethal conditions such as cold (cells frozen without special storage medium are killed; prolonged chilling is detrimental), heat, delays of several days in route (metabolizing cells must be given fresh nutrient medium periodically; this is usually impossible in transit), or inadvertent positioning of cultures so that nutrient medium does not cover the cells (see the discussion by Paul, supra on the problems of transporting cell cultures). The occasional practice of filling cultures with nutrient medium to solve this problem adds great weight and consequently increases the expense of shipping if significant distances are involved, (cell cultures are usually shipped by air).

Spillage of medium from culture vessels not completely sealed, such as depression or Petri plates, make successful shipping of cell cultures growing in such vessels presently very difficult. Thus, it is an objective of this invention to widen the variety of culture vessels available for use with cell cultures which are to be shipped from one place to another. According to this invention, the medium overlaying the cells is in a phase and/or in such a small quantity that there is no problem of spillage or leakage from unsealed culture vessels, regardless of the position in which the vessels are placed during transit.

Whereas surface adhering cell cultures, when shipped, must now be attended by trained personnel soon after arrival at their destination, such cells stored at low temperatures need only be refrigerated at their destination until trained personnel become available or it is otherwise convenient to care for the cultures. Accordingly, it is an objective of this invention that careful coordination in timing between shipper and recipient of living cells be less critical and that a tissue culture technician not be required to care for every shipment of cells immediately upon its arrival at a destination.

DESCRIPTION OF THE PREFERRED EMBODIMENTS

In the foregoing and the following description and discussion of this invention, the term "surface attached" refers to any living cells which naturally adhere to surfaces within culture vessels, or which can be made to adhere to such surfaces artificially.

The term "living cell cultures" or "living cells" in the sense used herein refers to any type of animal cell or group of cells which is maintained or is allowed to propagate artificially outside the animal of origin, in culture vessels. This includes cells which have no apparent organization (technically called "cell cultures") as well as groups of cells which retain degrees of organization resembling that seen in the original tissues or organs from which they were derived (technically called "tissue cultures" or "organ cultures"). The term "living cells", as used herein, is further defined to include: (1 cells which are infected naturally or artificially with living agents such as viruses, mycoplasma, rickettsia, bacteria or any other living agents; or (2) cells which have been treated physically or chemically so as to modify their normal characteristics or chemical composition. The only restriction implied is that cells be cooled and stored so that when they are revived some of the cells retain structural organization and can later carry out some or all of the metabolic processes usually associated with those cells before they were stored. "Living" in this sense does not, therefore, imply a requirement for indefinite cell division or a complete metabolic capability either before or after cooling and storage. In fact, cells may be infected or otherwise treated deliberately prior to preservation by the process herein described, so as to arrest or modify cell division or certain metabolic capabilities either temporarily or permanently; these treated or modified cells are included in the term "living cell cultures" used in this text.

Generally, the preferred process for cooling, storing and reviving living cell cultures, according to the present invention, comprises the steps of:

a. placing living cells of an appropriate type and concentration into culture vessels with a suitable cell culture medium and allowing the cells to adhere, or causing them by artificial means to adhere, to the vessels' surfaces (these are hereafter called "living cell cultures" or "living cells");

b. allowing the cells to multiply to a desired concentration per unit surface area, or otherwise to develop to a desired state, c. removing the cell culture medium from the culture vessels and replacing it with a medium containing about 10% dimethyl sulfoxide (by volume) and about 10% animal serum (hereafter this medium is called the "storage medium");

d. exposing the cells to the storage medium for a period of about 15 minutes (at temperatures ranging from about 20°C to about 25°C) to allow equilibration of this medium with the cells;

e. removing sufficient amounts of storage medium from the culture vessels to prevent later disturbance of surface-attached cells by movement during warming, yet retaining enough to form a layer of storage medium over the attached cells during the cooling process, f. lowering the temperature of the cell cultures in the culture vessels until a temperature of about −20°C or lower is reached, g. within a few hours, transferring the culture vessels and the cells therein to a container having a temperature of about −70°C or less, where the cells are kept until it is convenient to withdraw them for revival, h. warming the cell culture vessels and thereby the cells rapidly (for example, by exposure to water at about 37°C), being careful to minimize movement of fluid or ice over the culture surfaces and consequent disturbance of the surface-adhering living cells, i. removing the warmed storage medium from the living cell cultures by decanting or aspiration, j. replacing the storage medium with an appropriate cell culture medium (one usually used for culturing or maintaining that particular cell type), k. incubating the revived cell cultures under conditions known to be favorable for the culture or maintenance of that particular cell type.

It should be understood that the above general description and the following explanations are only examples of how the process of this invention can be carried out and are not to restrict the variety of ways that the main objectives might be achieved within the general scope of the invention.

COMPOSITION OF THE STORAGE MEDIUM

Any growth medium normally used for cell cultivation (growth) should be generally satisfactory as a base for preparing the storage medium. To this may be added sterile DMSO, glycerol or ethylene glycol to provide the appropriate concentrations. Hereinafter, concentrations of these three compounds are expressed as percents by volume; for example, a 10% concentration of DMSO in a storage medium is defined as consisting of 10 ml of DMSO and 90 ml of cell culture growth medium.

Cell types and strains vary in their ability to withstand the rigors of cooling, storage and revival as living cell cultures. It is understandable, therefore, that various cell types and strains differ in their optimal requirements concerning the composition of the storage medium. When several different cell types or strains are to be stored, it is technically more convenient to use a single storage medium whose composition is satisfactory, though perhaps not optimal for all the cells. Therefore, according to a preferred embodiment of this invention the storage medium may comprise about 10% DMSO in a cell culture growth medium containing about 5% to about 20% serum (such as fetal calf serum) with the remainder being an isotonic buffered solution (such as Basal Eagles medium with Earle's salts).

AMOUNT OF THE STORAGE MEDIUM TO BE USED

After exposing surface adhering living cells to the storage medium for a few minutes at room temperature, part to nearly all of this medium can be removed prior to cooling and storage. In accordance with the preferred embodiment of this invention, a depth of about 3mm to about 5mm overlay of storage medium gives favorable results, i.e., long term stability of viable cells. There are, however, at least two distinct advantages in removing most of the storage medium from the cell cultures after a few minutes exposure and just prior to cooling and storage: (1) growth or maintenance medium can be carefully placed in the culture vessel on a side not occupied by the storage medium-treated, surface adhering cells, the entire culture cooled in this position, stored, then warmed and rotated to a position so that the cells are covered with culture medium and can be incubated immediately without the necessity of opening the culture vessel to change fluids. Thus, a further technical simplification is accomplished and an even higher degree of uniformity is achieved in the stored, revived cultures by avoiding the use of different lots of growth or maintenance medium to nourish cell cultures revived at different times; and (2) there will be little or no disturbance of the adhering cells by rough handling during shipment or during warming (sudden movements of fluid and/or melting ice, if excessive, can dislodge cells). These advantages could not be achieved except for the discoveries: (a) that surface attached cells can be cooled, stored and revived with favorable recovery of cell viability and so as to retain their position of attachment on the surfaces to which they originally adhered; and (b) that such cells can be cooled, stored and successfully revived with very thin layers of storage medium bathing their surfaces.

RAPID COOLING OF CELLS TO BE STORED

In contrast to reportedly consistent failures to cool most suspended aminal cells rapidly and obtain satisfactory recovery of viable cells (Meryman, supra, erythrocytes are the exception), some types of surface attached living cells can be treated, according to the process of this invention, cooled rapidly, stored and satisfactory proportions of viable cells then recovered after warming. This can be accomplished, according to a preferred embodiment of this invention, by exposing the surface attached living cell cultures to storage medium for about 15 minutes, removing all but a thin layer of medium by aspiration or decanting, placing the cell cultures directly (without insulation around the culture vessels) into a low temperature refrigeration unit, allowing the cultures to cool, then storing the cultures at a low temperature indefinitely. When electric refrigeration is not available, or if stored cell cultures are to be packaged and shipped soon, the vessels can be placed directly into an insulated box with carbon dioxide ice for the initial rapid cooling and for subsequent storage. Care must be exercised, of course, to insure that culture vessels are gas-tight when exposed to carbon dioxide, to prevent excessive lowering of the pH in the cell culture. One of the unexpected benefits of the discovery that surface adhering cells can be frozen and stored in place is that they can be frozen rapidly without severe losses in viable cells.

SLOW COOLING OF CELLS TO BE STORED

Surface-attached living cells can also be cooled slowly and somewhat more satisfactory proportions of viable cells recovered after warming. This can be accomplished with sophisticated instrumentation or by placing insulation of a predetermined optimal thickness (such as polystyrene foam having a thickness of about one inch) around a given number of the culture vessels containing the surface attached living cells so as to cause slow cooling when the cell cultures (overlayed with storage medium) are placed in a low temperature refrigeration unit (See similar descriptions by Paul, supra, and Wasley and May, supra). According to a preferred embodiment of this invention, the storage medium contains about 10% DMSO and about 10% serum. Insulation around the cooled vessels (whether cooled slowly or rapidly) seems to be particularly valuable after cooling to prevent sudden temperature changes within the cell culture vessels when the refrigeration unit is opened periodically or the vessels are transferred to other refrigeration units (such temperature fluctuations are unfavorable for maintaining storage of viable cells). A preferred embodiment of this invention is the insulation of surface attached living cell cultures with that amount of insulation found in practice to give a cooling rate within the culture vessels of about 0.5° to 1°C per minute when the insulated vessels containing the living cells and storage medium are placed in a suitable refrigeration unit. For example, one inch of polystyrene insulation around a small number of cell culture vessels will allow approximately this rate of temperature decrease to occur (between about −10°C and −25°C) when the insulated vessels are placed in a refrigeration unit having a temperature of approximately −70°C. Cooling by this method usually does not give a perfectly linear cooling rate over the entire cooling range, but the results are quite satisfactory. It is probable that one of the chief advantages of placing insulation around cell cultures for storage is the buffering effect against temperature fluctuations during long term storage, in addition to or rather than the slow cooling effect achieved initially.

TEMPERATURE AT WHICH CELLS CAN BE STORED SATISFACTORILY

Following initial cooling of surface attached living cells in the presence of storage medium, the cells can be stored at various temperatures ranging from about 0°C to less than −200°C, with varying degrees of efficiency. Lower (colder) temperatures are usually more satisfactory for long term storage, but storage can be accomplished, according to the process of this invention, at temperatures above (warmer than) −70°C. For example, some types of surface adhering living cells can be stored at −20°C for several weeks if a high recovery rate of viable cells is not essential (Scherer and Hoogasian, supra).

This invention is concerned with a process for cooling, storing and reviving living cell cultures which are attached to surfaces within the culture vessels. It is expected, of course, that those familiar with these disclosures and skilled in the art of cell culture can make useful modifications regarding the details of this process within the scope of the foregoing descriptions and the following claims without departing substantially from the basic principles described.

EXAMPLE

1. Living cells (hereafter called "cells") are made to detach from the surfaces upon which they have been cultured. This is done by scraping, mechanical agitation or by treatment with solutions of enzymes (such as 0.2% trypsin) or chelating agents (such as EDTA).

2. Suspended cells are counted in a hemacytometer, pelleted by low speed centrifugation (about 2,000 × gravity for 5 minutes), and resuspended in an appropriate cell culture growth medium (as described by Paul, supra or Wasley and May, supra) to give a concentration of about 100,000 cells per ml. Lesser concentrations (25,000 – 50,000 cells per ml) may be used in the case of rapidly growing cells; greater concentrations may be used in the case of slow growing cells, or when a rapid outgrowth of cells to a high density is desired.

3. Cell suspensions are dispensed into the type or types of culture vessels most convenient for the purposes intended, in volumes appropriate to the size of the vessels. Examples of vessels are test tubes (about 1–2 ml. cell suspension per tube), multi-depression plastic trays (about 0.2–2 ml cell suspension per depression), glass or plastic bottles (5–100 ml cell suspension per bottle) or Petri type plates (1–5 ml cell suspension per plate).

4. Cells in the culture vessels are incubated at a temperature optimal for the cell type (about 37°C for many mammalian cells and 20°–29°C for fish and reptile cells). In the case of unsealed vessels, a gaseous atmosphere having a composition favorable for cell culture is provided (a favorable atmosphere usually contains about 5% $CO_2$ and a high humidity).

5. Cells are incubated for periods of time sufficient to allow cell attachment to the surfaces within the vessel, and to allow sufficient cell division to give a concentration of cells suitable for use in specific types of work (this may vary from a sparse, low density outgrowth of cells to a crowded, continuous sheet of cells).

6. The growth medium is drained or aspirated from the cell culture vessel, and replaced with a "storage medium" containing about 10% by volume dimethyl sulfoxide prepared in cell culture growth medium. The volume of "storage medium" is variable, but at minimum, the volume must be sufficient to bathe the attached cells.

7. The "storage medium" is allowed to bathe the cells for about 15 minutes before proceeding with the cooling procedure.

8. The "storage medium" may then be removed by draining or by aspiration, in the case of glass culture vessels or substrates, leaving only that "storage medium" which naturally adheres to the cell surfaces. Alternatively, "storage medium" can be left in the culture vessels to bathe the attached cells. The latter is optional when cells are cultured and adhered on glass substrates but is preferred when the cells are adhered to plastic surfaces.

9. The groups of cell culture vessels are then placed in an insulated container or, alternatively, the vessels are individually wrapped with insulating material. The insulated vessels are placed in a refrigeration unit, such as a −70°C freezer. If the culture vessels contain a significant volume of the "storage medium", the vessels are oriented in the freezer so as to allow the "storage medium" to bathe the cells. The cell culture vessels containing the surface attached cells are then cooled slowly (at about 0.5°–1°C per minute) so as to reach a temperature below −40°C. Alternatively, but less preferred, cell cultures with thin layers of "storage medium" can be placed into a refrigeration unit without insulation and frozen more rapidly.

10. The frozen cell cultures are kept in storage at a low temperature indefinitely. Temperatures lower than −60°C are preferred for long term storage. Temperature fluctuations in the refrigeration unit are to be avoided.

11. The cell culture vessels containing the surface adhered cells are withdrawn from storage when needed, insulation (if present) removed from the vessels and vessels warmed rapidly to a temperature of about 37°C to 41°C. This is done by exposing the vessels to warm water, a warm surface or moving warm air. Sudden or excessive movements of the vessels during the thawing process should be avoided to prevent pieces of ice and moving fluid from dislodging attached cells.

12. The thawed "storage medium" is drained or aspirated from the culture vessel, a cell culture growth medium is added gently in appropriate volumes (see item 3) and the cell cultures are incubated and/or used as desired. Ideally, cell culture vessels should not be agitated mechanically by bumping or by shaking excessively after growth medium is added, until the cultures have incubated for a few hours (12–24) and have resumed their normal metabolic activity.

13. Types of cells which have been successfully stored by this method include human embryonic brain cells, human embryonic lung cells, canine kidney cells, human amnion cells, monkey kidney cells and various human epithelial cell lines, both neoplastic and non-neoplastic.

I claim:

1. In a process for cooling, storing and reviving surface attached living cultured cells, the steps of:
   exposing living cultured cells which are attached to a surface of a storage vessel to a storage medium which is relatively non-toxic to such cells and which is compatible therewith during cooling to a temperature below 0°C, storage and subsequent warming processes;
   cooling said vessel and the surface attached living cells therein to a storage temperature below 0°C effective for arresting the metabolism of the cells; and
   storing said vessel and said surface attached cells at said storage temperature for an extended period of time.

2. A process as set forth in claim 1 wherein said storage medium contains about 5 to about 40% dimethyl sulfoxide.

3. A process as set forth in claim 2 wherein said storage medium contains approximately 10% dimethyl sulfoxide.

4. A process as set forth in claim 3 wherein said cooling is effectuated at a rate of about 1°C per minute.

5. A process as set forth in claim 4 wherein said storage temperature is about −70°C.

6. A process as set forth in claim 2 wherein said storage medium contains approximately 10% glycerol.

7. A process as set forth in claim 6 wherein said cooling is effectuated at a rate of about 1°C per minute.

8. A process as set forth in claim 7 wherein said storage temperature is about −70°C.

9. A process as set forth in claim 2 wherein said storage medium contains approximately 10% ethylene glycol.

10. A process as set forth in claim 9 wherein said cooling is effectuated at a rate of about 1°C per minute.

11. A process as set forth in claim 10 wherein said storage temperature is about −70°C.

12. A process as set forth in claim 1 wherein said storage medium contains about 5 to about 40% glycerol.

13. A process as set forth in claim 1 wherein said storage medium contains about 5 to about 40% ethylene glycol.

14. A process as set forth in claim 1 wherein said cooling is effectuated at a rate of about 1°C per minute.

15. A process as set forth in claim 14 wherein said storage temperature is about −70°C.

16. A process as set forth in claim 1 wherein said storage temperature is about −70°C.

17. A process as set forth in claim 1 wherein said storage medium is present in at least a sufficient quantity to completely wet the outer surfaces of said surface attached living cells.

18. A process as set forth in claim 17 wherein said storage medium is present in that quantity only which adheres to said surface attached living cells by surface phenomena after decanting or aspiration of said storage vessel.

19. A process as set forth in claim 1 wherein said cooling comprises placing non-insulated storage vessels containing said surface attached living cells directly into a refrigerated space maintained at said storage temperature.

20. A process as set forth in claim 1 wherein said storage temperature is in the range of about 0°C to about −200°C.

21. A process as set forth in claim 1 wherein, subsequent to said storage step, said vessel and the surface attached cells therein are warmed sufficiently to thaw said cells.

* * * * *